United States Patent [19]

Mohacsi et al.

[11] Patent Number: 4,912,102
[45] Date of Patent: Mar. 27, 1990

[54] ANALOGS OF NAPHTHO[1,2-β][1,4] THIAZEPIN-4(5H)-ONE

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 286,789

[22] Filed: Dec. 22, 1988

Related U.S. Application Data

[63] Continuation-in-part of Ser. No. 229,521, Aug. 5, 1988, abandoned, which is a continuation of Ser. No. 150,605, Feb. 1, 1988, abandoned.

[51] Int. Cl.⁴ .................. A61K 31/55; C07D 281/02
[52] U.S. Cl. ..................................... 514/211; 540/488
[58] Field of Search ........................ 514/211; 540/488

[56]   References Cited

U.S. PATENT DOCUMENTS 4,652,561  3/1987  Mohacsi ............................ 540/488

FOREIGN PATENT DOCUMENTS 128462A  6/1983  European Pat. Off. ............ 540/491
2143532A  2/1985  United Kingdom ................ 540/491

*Primary Examiner*—Robert T. Bond
*Attorney, Agent, or Firm*—George M. Gould; Bernard S. Leon; Matthew Boxer

[57]  ABSTRACT (+)—Cis compounds of the formula

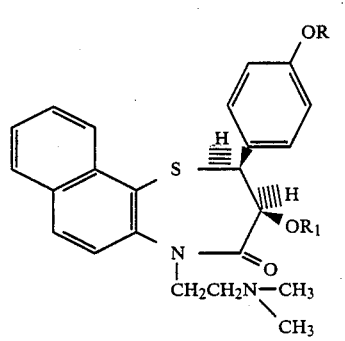

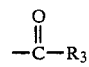

wherein R is lower alkyl; $R_1$ is $$-\overset{O}{\underset{\|}{C}}-R_3$$

wherein $R_3$ is pyridyl,

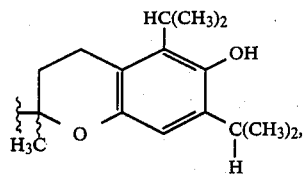

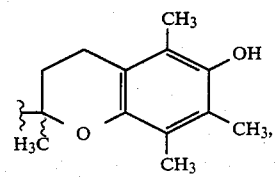

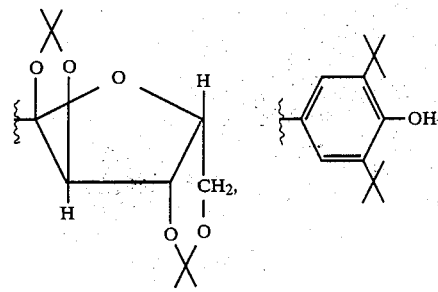

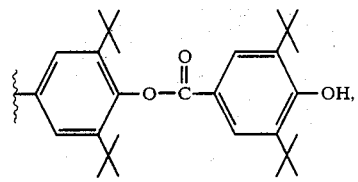

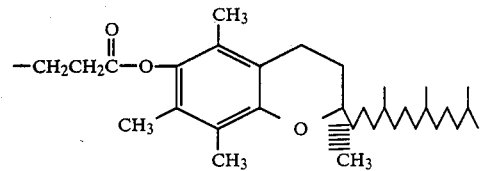

or phenyl unsubstituted or substituted by up to 3 substituents selected from the group consisting of hydroxy, halogen, lower alkoxy, and lower alkanoyloxy;

(−)cis enantiomers, and (±)—cis racemates thereof; or pharmaceutically acceptable acid addition salts thereof are described.

28 Claims, No Drawings

ANALOGS OF NAPHTHO[1,2-β] [1,4] THIAZEPIN-4(5H)-ONE

RELATED APPLICATIONS

This is a continuation-in-part of Ser. No. 229,521, filed Aug. 5, 1988, which in turn is a continuation of Ser. No. 150,605 filed Feb. 1, 1988, both now abandoned.

BRIEF SUMMARY OF THE INVENTION

The invention relates to (+)-cis compounds of the formula

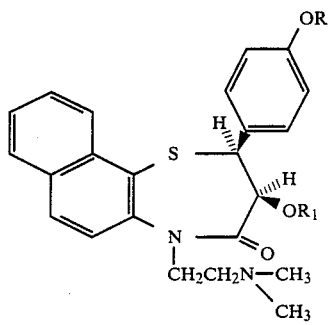

wherein R is lower alkyl; $R_1$ is

wherein $R_3$ is pyridyl,

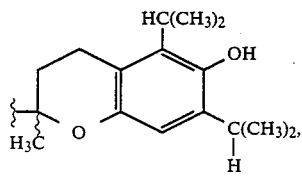

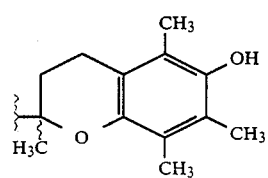

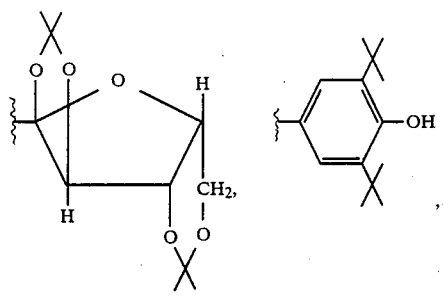

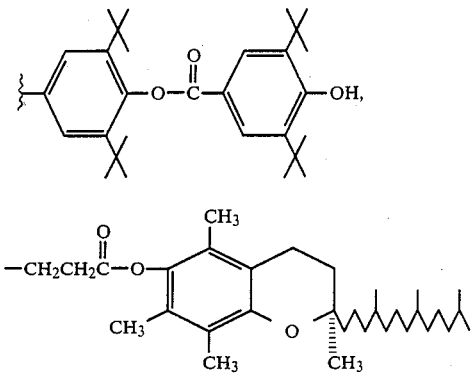

or phenyl unsubstituted or substituted by up to 3 substituents selected from the group consisting of hydroxy, halogen, lower alkoxy, and lower alkanoyloxy;

(−)-cis enantiomers, and (±)-cis racemates thereof; or pharmaceutically acceptable acid addition salts thereof.

Certain compounds of formula I are active as calcium channel blockers, and accordingly are useful as agents for treating ischemia and as agents for lowering blood pressure. Certain compounds of the invention are also useful as agents for inhibiting lipid peroxide formation.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl and the like. The term "lower alkoxy" denotes a straight or branched-chain lower alkoxy group containing 1 to 4 carbon atoms, for example, methoxy, ethoxy, propoxy, isopropoxy, butoxy and the like. The term "halogen" denotes the halogens, that is, bromine, chlorine, fluorine and iodine. The term "lower alkanoyloxy" denotes a straight or branched-chain alkanoyloxy group of 2 to 5 carbon atoms, for example, acetyloxy, propionyloxy, butyryloxy, isopropionyloxy and the like.

As used in the formulas herein a solid line (—■) indicates a substituent that is above the plane of molecule, and a dotted line ( ⁞⁞⁞⁞ ) indicates a substituent that is below the plane of the molecule. A wavy line (∼∼) indicates that the stereochemistry of the substituent is unknown, or that the molecule is epimeric at this position.

The invention relates to (+)-cis compounds of the formula

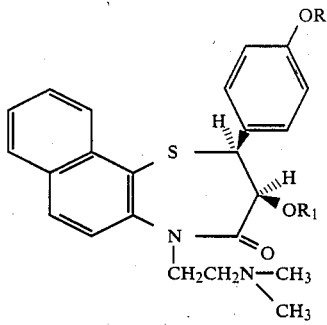

wherein R is lower alkyl; R₁ is

wherein R₃ is pyridyl,

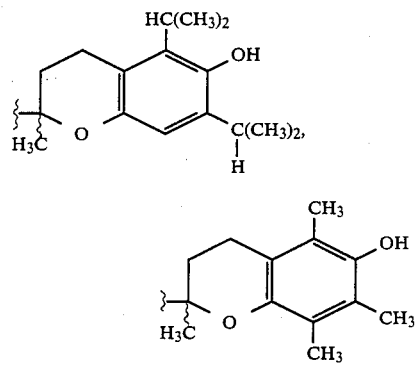

or phenyl unsubstituted or substituted by up to 3 substituents selected from the group consisting of hydroxy, halogen, lower alkoxy, and lower alkanoyloxy;

(−)-cis enantiomers, and (±)-cis racemates thereof or pharmaceutically acceptable salts thereof.

Certain compounds of formula I are active as calcium antagonists, that is, calcium channel blockers, and accordingly and are useful as agents for lowering blood pressure, as agents for treating ischemia. Certain compounds of formula I are also useful as agents for inhibiting lipid peroxide formation.

As used herein, the term "cis" denotes a compound wherein the substituted phenyl and —OR₁, substituents are both on the same side of the sulfur and nitrogen containing ring. As used herein, the term "(+)-cis" denotes an enantiomer having an absolute configuration analogous to that of (2S,3S)-2,3-dihydro-3-hydroxy-2-(4-methoxyphenyl)-5-[2-(dimethylamino)ethyl]naphtho[1,2-b][1,4]thiazepin-4(5H)-one.

A compound of the formula

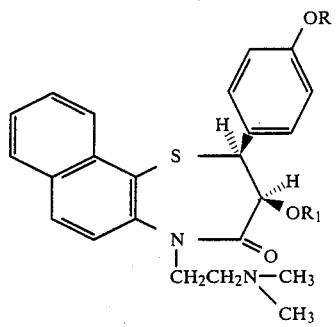

wherein R, and R₁ are as described above is a (+)-cis compound of the invention.

A compound of the formula

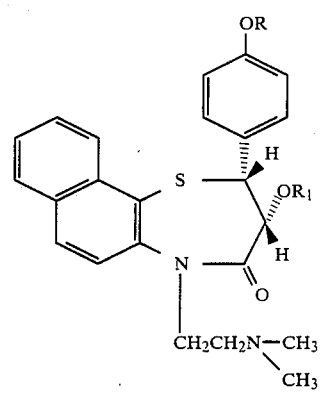

wherein R, R₁ are as described above is a (−)-cis compound of the invention.

Especially preferred compounds of the invention are (+)-cis compounds.

Other preferred compounds of the invention are those wherein R is methyl; R₁ is

wherein R₃ is phenyl substituted by up to 3 substituents selected from the group consisting of nitro, hydroxy, halogen, lower alkoxy, and lower alkanoyloxy. Of these, as has been pointed out above, (+)-cis compounds are especially preferred.

Most preferred compounds of the invention are those wherein R is methyl, R₁ is

wherein R₃ is phenyl substituted by two substituents selected from the group consisting of hydroxy, methoxy, and acetyloxy. Of these, as has been pointed out above, (+)-cis compounds are especially preferred.

Compounds of formula I include isomeric mixtures

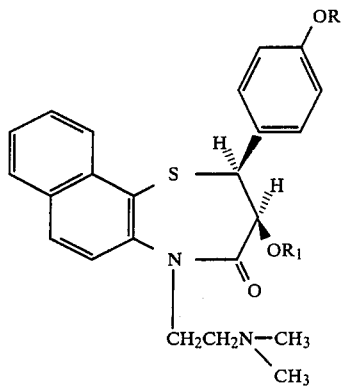

wherein R is lower alkyl, $R_1$ is

and $R_3$ is

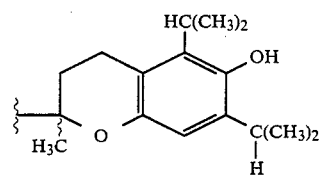

that is, wherein $R_3$ is

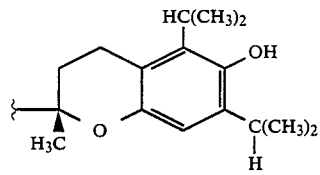

and

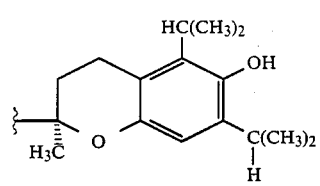

Of course, the (−)-cis enantiomers, and (±)-cis racemates thereof are included in the invention.

Compounds of formula I include isomeric mixtures

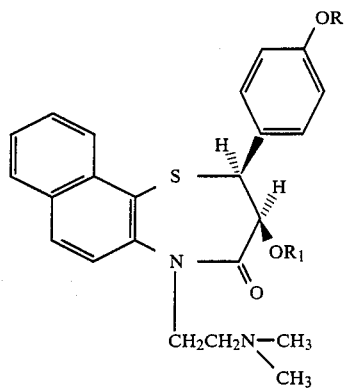

wherein R is lower alkyl, $R_1$ is

and $R_3$ is

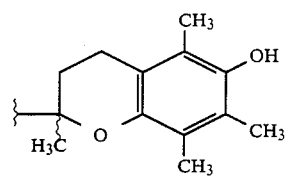

that is, wherein $R_3$ is

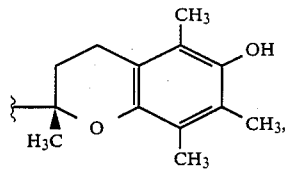

and

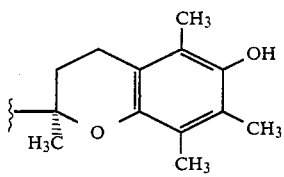

Of course, the (−)-cis enantiomers and (±)-cis racemates thereof are included in the invention.

Exemplary of compounds of formula I are:
(±)-cis-3-[(3,4-dimethoxybenzoyl)oxy]-2,3-dihydro-5-[2-(dimethylamino)ethyl]-2-(4-methoxyphenyl)naphtho[1,2-b][1,4]thiazepin-4(5H)-one;
(±)-cis-3-[[(2-acetyloxy)benzoyl]oxy]-2,3-dihydro-5-[2-(dimethylamino)ethyl]-2-(4-methoxyphenyl)naphtho[1,2b][1,4]thiazepin-4(5H)-one;
(±)-cis-2,3-dihydro-3-[(2-hydroxybenzoyl)oxy]-5-[2-(dimethylamino)ethyl]-2-(4-methoxyphenyl)naphtho[1,2-b][1,4]thiazepin-4(5H)-one;
(±)-cis-2-[[3,4-bis(acetyloxy)benzoyl]oxy]-5-[2-(dimethylamino)ethyl]-2-(4-methoxyphenyl)naphtho[1,2b][1,4]thiazepin-4(5H)-one;

(±)-cis-2,3-dihydro-3-[(3,4-dihydroxybenzoyl)oxy]-5-[2-(dimethylamino)ethyl]-2-(4-methoxyphenyl)naphtho[1,2-b][1,4]thiazepin-4(5H)-one;

(±)-cis-2,3-dihydro-2-(4-methoxyphenyl)-3-[(3,4,5-trimethoxybenzoyl)oxy]-5-[2-(dimethylamino)ethyl]-naphtho[1,2-b][1,4]thiazepin-4(5H)-one;

(±)-cis-2,3-dihydro-3-[4-[[[4-hydroxy-3,5-bis(1,1-dimethylethyl)benzoyl]oxy]bis-3,5-(1,1-dimethylethyl)-benzoyl]oxy]-5-[2-(dimethylamino)ethyl]-2-(4-methoxyphenyl)naphtho[1,2-b][1,4]thiazepin-4(5H)-one;

(+)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one;

(+)-cis-[2R-[2R*(4R*,8R*)]]-butanedioic acid 3,4-dihydro-2,5,7,8-tetramethyl-2-(4,8,12-trimethyltridecyl)-2H-1-benzopyran-6-yl-2,3,4,5-tetrahydro-3-hydroxy-2-(4-methoxyphenyl)-5-[2-(dimethylamino)ethyl]-4-oxonaphtho[1,2-b][1,4]thiazepin-3-yl ester;

(−)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one;

[(±)-cis-3(2alpha or 2beta)]-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one, called isomer "A" and which has 128°-130° mp for the (E)-2-butenedioate salt.

[(±)-cis-3(2alpha or 2beta)]-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one, called isomer "B" and which has 184°-185° mp for the hydrochloride salt.

(±)-cis-2,3-dihydro-2-(4-methoxyphenyl)-5-[2-(dimethylamino)ethyl]-3-[(3-pyridinylcarbonyl)oxy]naphtho[1,2-b][1,4]thiazepin-4(5H)-one;

[(+)-cis-3(2alpha, or 2beta)]-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one called isomer "B" which has a 200°-201° mp and $[\alpha]_D^{25} = -75.67°$(C. 0.91 MeOH); as the base, a 134°-136° mp and $[\alpha]_D^{25} -64.67°$(C. 1.00, MeOH) as the (E)-2-butenedioate salt.

The corresponding isomer, called isomer "A", has 150°-151° mp and $[\alpha]_D^{25} = -58.52°$(C. 0.978, MeOH) for the (E)-2-butenedioate salt, with $[\alpha]_D^{25} = -74.31°$(C. 1.03 MeOH) for the free base.

[(+)-cis-3(2alpha and 2beta)]-2,3-dihydro-3-[[(3,4-dihydro-6-hydroxy-2,5,7,8-tetramethyl-2H-1-benzopyran-2-yl)carbonyl]oxy]-2-(4-methoxyphenyl)-5-[2-(dimethylamino)ethyl]naphtho[1,2-b][1,4]thiazepin-4(5H)-one and (+)-cis-2,3-dihydro-3-[[(tetrahydro-2,2,5,5-tetramethyl-7H-dioxolo[4,5]furo[3,2-d][1,3]dioxin-3a-yl)carbonyl]oxy]-2-(4-methoxyphenyl)-5-[2-(dimethylamino)ethyl]naphtho[1,2-b][1,4]thiazepin-4(5H)-one.

(+)-Cis compounds of formula

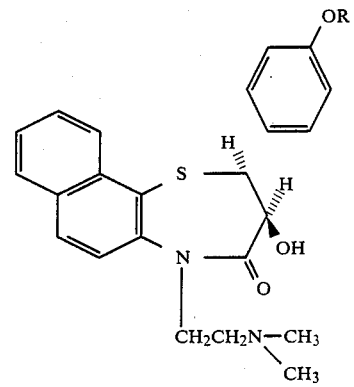

wherein R is as described above, (−)-cis enantiomers, and (±)-cis racemates thereof, are disclosed in U.S. Pat. No. 4,652,561, or can be prepared by methods analogous to those set forth in U.S. Pat. No. 4,652,561.

(+)-cis compounds of formula VIII, (−)-cis enantiomers, or (±)-cis racemates mixtures can be converted into corresponding (+)-cis compounds of the formula

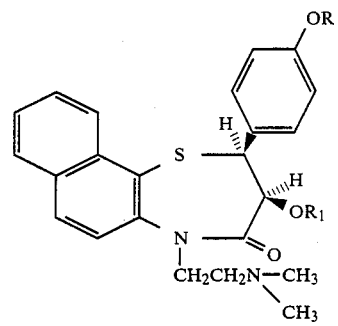

wherein R and $R_1$ are as described above or the corresponding (−)-cis compounds or (±)-cis racemates by methods described herein.

Specifically, a compound of formula VIII can be reacted with the desired acylating agent, such as, for example, 3,4-dimethoxybenzoyl chloride in an organic solvent such as collidine or more preferably pyridine, at about −10° C. to about 5° C., to yield a compound of formula I.

It is understood that different acylating agents are used to obtain different compounds of formula I. Exemplary of other acylating agents which may be used are 2-acetoxybenzoyl chloride; and 3,4,5-trimethoxybenzoyl chloride.

Alternatively, a compound of formula VIII can be reacted with an organic acid, $R_3COOH$, in the presence of a condensation catalyst such as 1,1'-carbonyldiimidazole or 1,3-dicyclohexylcarbodiimide wherein $R_3$ is as described above, in a suitable organic ether solvent such as dimethoxyethane, diethyl ether, or more preferably, tetrahydrofuran, at about 20° to 30° C., to yield the corresponding compound of formula I.

Or, a compound of formula VIII can be reacted with an organic acid, $R_3COOH$, wherein $R_3$ is described above, in the presence of a condensation catalyst such as 1,1'-carbonyldiimidazole or 1,3-dicyclohexylcarbodiimide, in an alkyl halide solvent such as carbon tetrachloride, chloroform, or, more preferably, methylene chloride at about $-5°$ C. to $10°$ C. to give a compound of formula I. Compounds of formula I wherein $R_3$ is lower alkanoyloxy substituted phenyl can be converted to the corresponding hydroxy substituted compounds by hydrolyzing the alkanoyloxy group by known methods.

The compounds of formula I, including the pharmaceutically acceptable acid addition salts thereof, are calcium antagonists, that is, calcium channel blockers, and are therefore useful as agents in lowering blood pressure and in treating ischemia. They are also useful as agents for inhibiting lipid peroxide formation. The pharmacologically useful activities of certain compounds of formula I in the specific tests listed below are demonstrated in warm-blooded animals using standard procedures that are set forth.

GUINEA PIG ILEUM ASSAY

Male guinea-pigs weighing from 300–400 grams were stunned and bled. The abdomen was opened and 10–15 cm of terminal ileum was carefully removed and cleaned and placed in Tyrode's Solution of the following composition: NaCl (8 g/l), KCl (0.2 g/l), $MgCl_2$ (0.1 g/l), $CaCl_2$ (0.2 g/l). $NaH_2PO_4$ (0.05 g/l), $NaHCO_3$ (1.0 g/l) and Glucose (1 g/l). The solution was maintained at $37°$ C. and gassed with 95% $O_2$ and 5% $CO_2$. Portions of the ileum were placed over a glass rod, a shallow incision was made the length of the mesenteric attachment just severing the outer-longitudinal muscle layer. The longitudinal muscle was separated from the underlying circular muscle by gentle dissection (Rang. H. P. Annals. of New York Academy of Science, vol. 144, page 756, 1964). The tissue was fixed at one end to a tissue holder, the other end was connected by a thread to a force transducer and suspended in a muscle bath containing Tyrode's Solution maintained at $37°$ C. and gassed with 95% $O_2$ and 5% $CO_2$. An initial tension of 500 mg was applied and the tissue allowed to equilibrate for 60 minutes prior to the start of the study. During this period the tissue was washed every 16 minutes. Each preparation, at 16 minute intervals, was challenged with KCl sufficient to yield a bath K+ concentration of 80 mMK for 2 minutes, then washed with fresh solution. The 16 minute interval between K+ challenges was maintained throughout the study. Upon stabilization of the responses to the K+ challenge the test compound (potential calcium entry antagonist) was introduced into the bath 2 minutes prior to and during the 2 minute exposure to K+ after which the bath was cleared and washed with fresh solution. Logarithmically increasing doses (up to $10^{-4}M$) of the potential antagonist were administered as the study progressed.

The measure of a compound's ability to inhibit the tonic contraction of muscle is a measure of its activity as a calcium channel blocking agent.

The $IC_{50}$ is that concentration at which a compound inhibits the tonic contraction of muscle by 50%.

The activity of compounds of the invention in this test is given in the table which follows.

TABLE 1

| Inhibition of K+-Induced Contractile Responses In The Guinea Pig Ileal Longitudinal Smooth Muscle $IC_{50}$'s | |
|---|---|
| Compound | Tonic |
| C | $7.0 \times 10^{-6}$ |

TABLE 1-continued

| Inhibition of K+-Induced Contractile Responses In The Guinea Pig Ileal Longitudinal Smooth Muscle $IC_{50}$'s | |
|---|---|
| Compound | Tonic |
| D | $3.5 \times 10^{-6}$ |
| E | $1.3 \times 10^{-5}$ |
| F | $4.5 \times 10^{-5}$ |
| J | $7.0 \times 10^{-5}$ |
| M | $1.6 \times 10^{-5}$ |

In the tables, herein, Compound C is (+)-cis-2,3-dihydro-3-Hydroxy-5-[2-methyl-amino]ethyl]-2-(4-methyloxyphenyl)naphtho[1,2-b][1,4]thiazepin-4(5H)-one (E)-2-butenedioate as the semihydrate;

Compound D is (+)-cis-3-(acetyloxy)-2,3-dihydro-2-(4-methyl-oxyphenyl)-5-[2-methylamino)ethyl]naphtho[1,2-b][1,4]thiazepin-4(5H)-one (E)-2-butenedioate as the semihydrate;

Compound E is (±)-cis-3-[[(2-acetyloxy)benzoyl]oxy]-2,3-dihydro-5-[2-(dimethylamino)ethyl]-2-(4-methoxyphenyl)naphtho[1,2-b][1,4]thiazepin-4(5H)-one hydrochloride;

Compound F is (±)-cis-2,3-dihydro-3-[(2-hydroxybenzoyl)oxy]-5-[2-(dimethylamino)ethyl]-2-(4-methoxyphenyl)naphtho[1,2-b][1,4]thiazepin-4(5H)-one hydrochloride;

Compound J is (±)-cis-2,3-dihydro-2-(4-methoxyphenyl)-3-[(3,4,5-trimethoxybenzoyl)oxy]-5-[2-(dimethylamino)ethyl]naphtho [1,2-b][1,4]thiazepin-4(5H)-one hydrochloride as the semihydrate;

Compound M is (±)-cis-2,3-dihydro-2-(4-methoxyphenyl)-5-[2-(dimethylamino)ethyl]-3-[(3-pyridinylcarbonyl)oxy]naphtho[1,2-b][1,4]thiazepin-4(5H)-one dihydrochloride (4:5) hydrate; and;

[(+)-Cis-3(2α or 2β)]-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one (E)-2-butenedioate monohydrate (isomer "A"), and the corresponding "B" isomer, was not found to be active in this test, but was found to be active in the following anti-peroxidative activity test. As noted above, the melting point of the (E)-2-butenedioate salt of this isomer "B", was $134°–136°$; the melting point of the free base of this isomer "B" was $200°–201°$. Isomers "A" and "B" of the corresponding (±)-cis racemate were also found to be active in the latter test. As mentioned above, the mp of the (E)-2-butenedioate salt of isomer "A" of the (±)-cis racemate was $128°–130°$, and the mp of the hydrochloride salt of isomer "B" of the (±)-cis racemate was $184°–185°$.

The following compounds of the invention were not found to be active in the guinea pig ileum test, but were active in the anti-peroxidative test:

(±)-cis-2,3-dihydro-3-[[4-hydroxy-3,5-bis(1,1-dimethylethyl)benzoyl]oxy]-2-(4-methoxyphenyl)-5-[2-(dimethylamino)ethyl]naphtho[1,2-b][1,4]thiazepin-4(5H)-one hydrochloride as the hydrate;

(±)-cis-2,3-dihydro-3-[(3,4-dimethoxy)benzoyl]oxy]-2-(4-methoxyphenyl)-5-[2-(dimethylamino)ethyl]naphtho[1,2-b][1,4]thiazepin-4(5H)-one as the semihydrate;

[(+)-Cis-3(2α or 2β)]-2,3-dihydro-3-[[3,4-dihydro-6-hydroxy-2,5,7,8-tetramethyl-2H-1-benzopyran-2-yl)carbonyl]oxy]-2-(4-methoxyphenyl)-5-[2-(dimethylamino)ethyl]naphtho[1,2-b][1,4]thiazepin-4(5H)-one semihydrate

ANTI-PEROXIDATIVE ACTIVITY

An in vitro assay system to measure antiperoxidative activity is done in two steps: (A) lipid peroxidation is triggered by a free-radical generating system that replicates the superoxide-dependent, iron-promoted Haber-Weiss reaction, and (B) peroxidation is measured spectrophotometrically as the production of malondialdehyde-like products (MDA). Liposomes prepared from the native rat cardiac lipid are incubated with hypoxanthine, xanthine oxidase, and Fe·ADP chelate, and a test substance or buffer in glass tubes for 60 minutes at 37° C. The amount of peroxidation is determined by adding a thiobarbituric acid-reaction mixture to the tubes, heating to 80° C. for 30 minutes and reading the pink adduct at 530 nm.

TABLE 2
Anti-Peroxidative Activity

[Structure: naphthalene-S-CH(H)-CH(p-methoxyphenyl)(H)-N(CH₂CH₂N(CH₃)₂)-C(=O)- with OCR₃ group] →

| $R_3$ | $IC_{50}$ (μM) | % Inhibition (1 μM) |
|---|---|---|
| [3,4-bis(OC(=O)CH₃)phenyl] | >1 | 15.6 |
| [chroman with C(CH₃)₂, OH, C(CH₃)₂, CH₃] | (±) <1 isomer "A" | 62.6 |
| [chroman with C(CH₃)₂, OH, C(CH₃)₂, CH₃] | (±) <1 isomer "B" | 66.7 |

TABLE 2-continued
Anti-Peroxidative Activity

[Structure: naphthalene-S-CH(H)-CH(p-methoxyphenyl)(H)-N(CH₂CH₂N(CH₃)₂)-C(=O)- with OCR₃ group] →

| $R_3$ | $IC_{50}$ (μM) | % Inhibition (1 μM) |
|---|---|---|
| [chroman with C(CH₃)₂, OH, C(CH₃)₂, CH₃] | (+) <1 isomer "A" | 58.5 |
| [chroman with C(CH₃)₂, OH, C(CH₃)₂, CH₃] | (+) <1 isomer "B" | 59.6 |
| [3,4-dimethoxyphenyl] (2R cis) | >1 | 13.1 |
| [3,4-dimethoxyphenyl] (2R cis) | >1 | 11.5 |
| [3,4,5-trimethoxyphenyl] | >1 | 12.8 |
| [3,5-di-tert-butyl-4-hydroxyphenyl] | >1 | 9.8 |

TABLE 2-continued

Anti-Peroxidative Activity

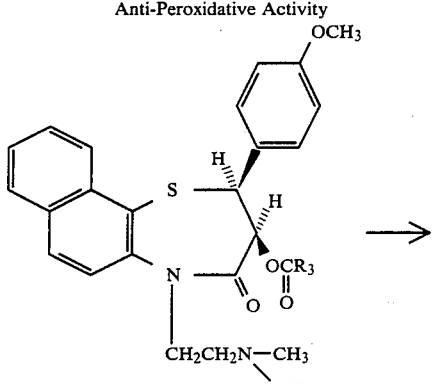

| R₃ | IC₅₀ (μM) | % Inhibition (1 μM) |
|---|---|---|
| 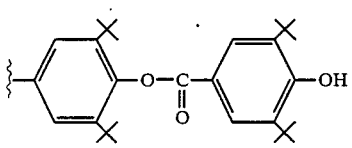 | >1 | 5.9 |

The compounds of formula I, and the pharmaceutically acceptable acid addition salts thereof, as herein described, can be incorporated into standard pharmaceutical dosage forms. The compounds of formula I are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in a liquid, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of inducing calcium antagonist activity in a warm-blooded animal in need of such treatment which comprises administering an effective amount of a compound of formula I. The invention also relates to a method of lowering blood pressure or treating ischemia by bringing about myocardial preservation during ischemia, which comprises administering an effective amount of a compound of formula I, or a pharmaceutically acceptable acid addition salt thereof to a warm-blooded animal in need of such treatment. The amount of an oral daily dosage can be determined by one skilled in the art and is comparable to that of dilitazem.

It is to be understood, however, that dosages may vary from individual to individual and accordingly the above recitation is not intended to limit the scope of the present invention in any way.

The following examples further illustrate the invention. All temperatures are in ° C., unless otherwise mentioned.

EXAMPLE 1

(+)-cis-3-(Acetyloxy)-5-[[2-[(2,2,2-trichloroethoxy)carbonyl]methylamino]ethyl]-2,3-dihydro-2-(4-methoxyphenyl)naphtho[1,2-b][1,4]thiazepin-4(5H)-one To a solution of 1.9 g (0.004 mol) of (+)-cis-2,3-dihydro-3-(acetyloxy)-2-(4-methoxyphenyl)-5-[2-(dimethylamino)ethyl]naphtho[1,2-b][1,4]thiazepin-4(5H)-one in 30 ml of dry benzene was added 0.1 g of powdered potassium carbonate followed by 4.8 g (0.022 mol) of trichloroethyl chloroformate. After the reaction mixture was stirred and refluxed for 17 hours, it was concentrated and the residue was partitioned between methylene chloride and 1N HCl. The aqueous solution was extracted with methylene chloride and the combined extracts were washed with brine, dried (MgSO₄) and the solvent was removed under reduced pressure. The crude product after crystallization from ether afforded 2.2 g (88%) of (+)-cis-3-(acetyloxy)-5-[[(2-[(2,2,2-trichloroethoxy)carbonyl]methylamino]ethyl]-2,3-dihydro-2-(4-methoxyphenyl)naphtho[1,2-b][1,4]thiazepin-4(5H)-one, mp 193°-194°, $[\alpha]_D^{25}$ +18.88° (C. 0.44, CHCl₃).

$C_{28}H_{27}Cl_3N_2O_6S$ (625.95); Calcd: C, 53.82; H, 4.35; N, 4.48. Found: C, 53.81; H, 4.31; N, 4.55.

EXAMPLE 2

(+)-cis-3-(Acetyloxy)-2,3-dihydro-2-(4-methoxyphenyl)-5-[2-(methylamino)ethyl]naphtho[1,2-b][1,4]thiazepin-4(5H)-one A solution of 2.0 g (0.0032 mol) of (+)-cis-3-(acetyloxy)-5-[[2-[(2,2,2-trichloroethoxy)carbonyl]methylamino]ethyl-2,3-dihydro-2-(4-methoxyphenyl)-naphtho[1,2-b][1,4]thiazepin-4(5H)-one in 60 ml of 90% acetic acid-water was chilled in an ice-water bath. To the mixture was added portion wise 1.6 g of zinc powder (60–200 mesh) over a period of 15 minutes then was stirred at this temperature for 5 hours. The reaction mixture was filtered and the filtrate was concentrated at reduced pressure. The residue was partitioned between ethyl acetate and cold dilute ammonium hydroxide. The combined ethyl acetate solutions were washed with brine, dried (MgSO₄) and concentrated to give the crude product, which was dissolved in ethyl acetate and chromatographed on a column using 45 g of silica gel. The column was eluted with 20 ml portions of ethyl acetate—methanol (90:10). Fractions 24-40 were combined and the solvent was removed to give 1.6 g (0.0035 mol) of base, which was dissolved in acetonitrile and treated with 0.4 g (0.0035 mol) of fumaric acid to afford after separation 1.2 g (67%) of (+)-cis-3-(acetyloxy)-2,3-dihydro-2-(4-methoxyphenyl)-5-[2-(methylamino)ethyl]naphtho[1,2-b][1,4]thiazepin-4(5H)-one (E)-2-butenedioate, mp 182°-183°, $[\alpha]_D^{25}$ −3.72° (C. 0.96, MeOH).

$C_{25}H_{26}N_2O_4S \cdot C_4H_4O_4$ (566.55) Calcd: C, 61.48; H, 5.34; N, 4.95. Found: C, 61.46; H, 5.43; N, 4.93.

A sample of the above salt, was dissolved in water and made basic with cold ammonium hydroxide. The aqueous suspension was extracted with ethyl acetate. The organic extracts were washed with brine, dried (MgSO₄) and concentrated. The residue was crystallized from a mixture of ethyl acetate—pet. ether to give (+)-cis-3-(acetyloxy)-2,3-dihydro-2-(4-methoxyphenyl)-5-[2-(methylamino)ethyl]naphtho[1,2][1,4]-thiazepin-4(5H)-one, mp 123°-124°, $[\alpha]_D^{25}$ −5.74° (C. 0.696, MeOH).

$C_{25}H_{26}N_2O_4S$ (450.47) Calcd: C, 66.65; H, 5.82; N, 6.22. Found: C, 66.41; H, 5.83; N, 6.14.

EXAMPLE 3

(+)-cis-2,3-Dihydro-3-hydroxy-5-[2-(methylamino)ethyl]-2-(4-methoxyphenyl)naphtho[1,2-b][1,4]thiazepin-4(5H)-one A solution of 0.4 g (0.00089 mol) of (+)-cis-3-(acetyloxy)-2,3-dihydro-2-(4-methoxyphenyl)-5-[2-(methylamino)ethyl]naphtho[1,2-b][1,4]thiazepin-4(5H)-one in a mixture of 10 ml of ethanol and 10 ml of 0.5M $K_2CO_3$ was heated at 70°–80° for one hour. The mixture was concentrated to a low volume under reduced pressure, diluted with water (saturated with NaCl) and extracted with ethyl acetate. The combined ethyl acetate solutions were washed with brine, dried ($MgSO_4$) and the solvent was removed. The residue, 0.25 g in acetonitrile, was treated with 0.08 g (0.0069 mol) of fumaric acid and the crystals were collected to afford 0.25 g (53%) of (+)-cis-2,3-dihydro-3-hydroxy-5-[2-(methylamino)ethyl]-2-(4-methoxyphenyl)naphtho[1,2-b][1,4]thiazepin-4(5H)-one (E)-2-butenedioate as the semihydrate, mp 178°–180° $[\alpha]_D^{25}$ +7.97° (C. 0.966, MeOH).

$C_{23}H_{24}N_2O_3S \cdot C_4H_4O_4 \cdot 0.5H_2O$ (533.51): Calcd: C, 60.78; H, 5.47; N, 5.25. Found: C, 61.04; H, 5.43; N, 5.81.

A sample of the above salt, was dissolved in water, basified with cold dilute ammonium hydroxide and the aqueous suspension was extracted with ethyl acetate. The combined ethyl acetate solutions were washed with brine, dried ($MgSO_4$) and the solvent was removed under reduced pressure. The residue was crystallized from ethyl acetate to give (+)-cis-2,3-dihydro-3-hydroxy-5-[2-(methylamino)ethyl]-2-(4-methoxyphenyl)naphtho[1,2-b][1,4]thiazepin-4(5H)-one as the semihydrate, mp 104°–105°, $[\alpha]_D^{25}$ +18.42° (C. 1.04, MeOH).

$C_{23}H_{24}N_2O_3S \cdot 0.5H_2O$ (417.44) Calcd: C, 66.17; H, 6.04; N, 6.71. Found: C, 66.19; H, 6.20; N, 6.33.

EXAMPLE 4

(±)-cis-3-[(3,4-Dimethoxybenzoyl)oxy]-2,3-dihydro-5-[2-(dimethylamino)ethyl]-2-(4-methoxyphenyl)naphtho[1,2-b][1,4]thiazepin-4(5H)-one To a solution of 2.0 g (0.0047 mol) of (±)-cis-2,3-dihydro-3-hydroxy-2-(4-methoxyphenyl)-5-[2-(2-(dimethylamino)ethyl]naphtho[1,2-b][1,4]thiazepin-4(5H)-one in 25 ml of pyridine (dried over KOH) was added portion wise 1.6 g (0.008 mol) of 3,4-dimethoxybenzoyl chloride over a period of 10 minutes at ice-bath temperature and the mixture was kept at this temperature overnight. It was concentrated to dryness and the residue was partitioned between ethyl acetate and dilute ammonium hydroxide. The combined ethyl acetate extracts were washed with brine and dried ($MgSO_4$). Removal of the solvent gave 2.9 g of a residue which was chromatographed on 45 g of silica gel and the column was eluted with 30 ml fractions of acetone. Fractions 8–18 were combined and the solvent was removed under reduced pressure to give 1.6 g of crude product, which was crystallized from ether to afford 0.9 g (32%) of (±)-cis-3-[(3,4-dimethoxybenzoyl)oxy]-2,3-dihydro-5-[2-(dimethylamino)ethyl]-2-(4-methoxyphenyl)naphtho[1,2-b][1,4]thiazepin-4(5H)-one, mp 182°–183°.

$C_{33}H_{34}N_2O_6S$ (586.68): Calcd: C, 67.56; H, 5.84; N, 4.78. Found: C, 67.59; H, 5.86; N, 4.84.

The above base, 0.90 g (0.00014 mol), was dissolved in acetone and acidified with hydrogen chloride (anhydrous) to afford 0.9 g (93%) of (±)-cis-3-[(3,4-dimethoxybenzoyl)oxy]-2,3-dihydro-5-[2-(dimethylamino)ethyl]-2-(4-methoxyphenyl)naphtho[1,2-b][1,4]thiazepin-4(5H)-one hydrochloride as the semihydrate, mp 226°–227°.

$C_{33}H_{34}N_2O_6S \cdot HCl \cdot 0.5 H_2O$ (632.18): Calcd: C, 62.69; H, 5.74; N, 4.43. Found: C, 62.55; H, 5.52; N, 4.38.

EXAMPLE 5

(±)-cis-3-[[(2-Acetyloxy)benzoyl]oxy]-2,3-dihydro-5-[2-(dimethylamino)ethyl]-2-(4-methoxyphenyl)naphtho[1,2-b][1,4]thiazepin-4(5H)-one To a solution of 2.0 g (0.0047 mol) of (±)-cis-2,3-dihydro-3-hydroxy-2-(4-methoxyphenyl)-5-[2-(dimethylamino)ethyl]naphtho[1,2-b][1,4]thiazepin-4(5H)-one in 25 ml of pyridine (dried over KOH) was added dropwise at ice-bath temperature 1.5 g (0.0075 mol) 2-acetoxybenzoyl chloride and the mixture was kept at this temperature overnight. It was concentrated at reduced pressure and the residue was partitioned between ethyl acetate and dilute ammonium hydroxide. The combined ethyl acetate solutions were washed with brine and dried ($MgSO_4$). Removal of the solvent gave 3.0 g of a residue which was crystallized from ethyl acetate to afford 1.7 g (63%) of (±)-cis-3-[[(2-acetyloxy)benzoyl]oxy]-2,3-dihydro-5-[2-(dimethylamino)ethyl]-2-(4-methoxyphenyl)naphtho[1,2-b][1,4]thiazepin-4(5H)-one, mp 141°–142°.

$C_{33}H_{32}N_2O_6S$ (584.60): Calcd: C, 67.80; H, 5.52; N, 4.79. Found: C, 67.79; H, 5.59; N, 4.85.

The above base, 1.7 g (0.0029 mol), in acetone was acidified with hydrogen chloride (anhydrous). The crystals were collected to give 1.6 g (89%) of (±)-cis-3-[[(2-acetyloxy)benzoyl]oxy]-2,3-dihydro-5-[2-(dimethylamino)ethyl]-2-(4-methyloxyphenyl)naphtho[1,2-b][1,4]thiazepin-4(5H)-one hydrochloride, mp 141°–142°.

$C_{33}H_{32}N_2O_6S \cdot HCl$ (621.10): Calcd: C, 63.81; H, 5.36; N, 4.51. Found: C, 63.50; H, 5.41; N, 4.42.

EXAMPLE 6

(±)-cis-2,3-Dihydro-3-[(2-hydroxybenzoyl)oxy]-5-[2-(dimethylamino)ethyl]-2-(4-methoxyphenyl)naphtho[1,2-b][1,4]thiazepin-4(5H)-one A solution of 0.6 g (0.001 mol) of (±)-cis-3-[[(2-acetyloxy)benzoyl]oxy]-2,3-dihydro-5-[2-(dimethylamino)ethyl]-2-(4-methoxyphenyl)naphtho[1,2-b][1,4]thiazepin-4(5H)-one in a mixture of 12 ml of acetone and 12 ml of 3N HCl was heated at reflux for 17 hours. The mixture was poured onto a mixture of ice and dilute ammonium hydroxide and the aqueous suspension was extracted with methylene chloride. The extracts were washed with water, then dried ($MgSO_4$) and removal of the solvent gave 0.40 g of crude product, which was crystallized from ethyl ether to afford 0.35 g (64%) of (±)-cis-2,3-dihydro-3-[(2-hydroxybenzoyl)oxy]-5-[2-(dimethylamino)ethyl]-2-(4-methoxyphenyl)naphtho[1,2-b][1,4]thiazepin-4(5H)-one, mp 150°–151°.

$C_{31}H_{30}N_2O_5S$ (542.63): Calcd: C, 68.62; H, 5.57; N, 5.16. Found: C, 68.52; H, 6.00; N, 4.92.

The above base, 0.35 g (0.0006 mol), in acetone was acidified with hydrogen chloride (anhydrous) to afford 0.35 g (95%) of (±)-cis-2,3-dihydro-3-[(2-hydroxybenzoyl)oxy]-5-[2-(dimethyl-amino)ethyl]-2-(4-methoxyphenyl)naphtho[1,2-b][1,4]thiazepin-4(5H)-one hydrochloride, mp 186°–188°.

$C_{31}H_{30}N_2O_5S \cdot HCl$ (579.13): Calcd: C, 64.29; H, 5.40; N, 4.83. Found: C, 64.26; H, 5.39; N, 4.87.

EXAMPLE 7

(±)-cis-2-[[3,4-bis(Acetyloxy)benzoyl]oxy]-5-[2-(dimethylamino)ethyl]-2-(4-methoxyphenyl)naphtho[1,2-b][1,4]thiazepin-4(5H)-one To a solution of 2.0 g (0.0047 mol) of (±)-cis-2,3-dihydro-3-hydroxy-2-(4-methoxyphenyl)-5-[2-(2-dimethylamino)ethyl]naphtho[1,2-b][1,4]thiazepin-4(5H)-one in 25 ml of pyridine (dried over KOH) was added portion wise 1.9 g (0.0075 mol) of 3,4-diacetoxybenzoyl chloride over a period of 10 minutes at ice bath temperature and the mixture was kept at this temperature overnight. It was concentrated at reduced pressure and the residue was partitioned between ethyl acetate and water. The combined ethyl acetate solutions were washed with brine and dried ($MgSO_4$). Removal of the solvent gave 3.3 g of crude product, which was boiled with 150 ml of ether. The insoluble material was filtered and the filtrate was concentrated and the residue was crystallized from ether to afford 0.5 g (17%) of (±)-cis-2-[[3,4-bis(acetyloxy)benzoyl]oxy]-5-[2-(dimethylamino)ethyl]-2-(4-methoxyphenyl)naphtho[1,2-b][1,4]thiazepin-4(5H)-one, mp 143°–144°.

$C_{35}H_{34}N_2O_8S$ (642.70): Calcd: C, 65.40; H, 5.33; N, 4.36. Found: C, 65.22; H, 5.36; N, 4.29.

To the above base, 0.5 g (0.0008 mol), was added 0.93 g (0.0008 mol) of fumaric acid. The mixture was dissolved in acetone. The resulting crystals were collected to afford 0.5 g (85%) of (±)-cis-2-[[3,4-bis(acetyloxy)benzoyl]oxy]-5-[2-(dimethylamino)ethyl]-2-(4-methoxyphenyl)naphtho[1,2-b][1,4]thiazepin-4(5H)-one (E)-2-butenedioate, mp 183°–184°.

$C_{35}H_{34}N_2O_8S \cdot C_4H_4O_4$ (758.77) Calcd: C, 61.73; H, 5.05; N, 3.69. Found: C, 61.42; H, 5.04; N, 3.82.

EXAMPLE 8

(±)-cis-2,3-Dihydro-3-[(3,4-dihydroxybenzoyl)oxy]-5-[2-(dimethylamino)ethyl]-2-(4-methoxyphenyl)naphtho[1,2-b][1,4]thiazepin-4(5H)-one To a solution of 2.0 g (0.0047 mol) of (±)-cis-2,3-dihydro-3-hydroxy-2-(4-methoxyphenyl)-5-[2-(2-dimethylamino)ethyl]naphtho[1,2-b][1,4]thiazepin-4(5H)-one in 25 ml of pyridine (dried over KOH) was added portion wise 1.9 g (0.0075 mol) of 3,4-diacetoxybenzoyl chloride over a period of 10 minutes at ice-bath temperature and the mixture kept at this temperature overnight. It was concentrated under reduced pressure and the residue was partitioned between ethyl acetate and dilute ammonium hydroxide. The ethyl acetate extracts were washed with brine and dried ($MgSO_4$). Removal of the solvent gave 3.0 g of crude product, which was crystallized from methanol to give 2.2 g (83%) of (±)-cis-2,3-dihydro-3-[(3,4-dihydroxybenzoyl)oxy]-5-[2-(dimethylamino)ethyl]-2-(4-methoxyphenyl)naphtho[1,2-b][1,4]thiazepin-4(5H)-one, mp 146°–148°.

$C_{31}H_{30}N_2O_6S$ (558.57) Calcd: C, 66.45; H, 5.41; N, 5.02. Found: C, 66.41; H, 5.53; N, 5.08.

The above base, 2.2 g (0.0039 mol) in methanol was acidified with hydrogen chloride (anhydrous). The crystals were separated by filtration to give 2.1 g (89%) of (±)-cis-2,3-dihydro-3-[(3,4-dihydroxybenzoyloxy]-5-[2-(dimethylamino)ethyl]-2-(4-methoxyphenyl)naphtho[1,2-b][1,4]thiazepin-4(5H)-one hydrochloride semihydrate, mp 198°–199°.

The above base, 2.2 g (0.0039 mol) in methanol was acidified with hydrogen chloride (anhydrous). The crystals were separated by filtration to give 2.1 g (89%) of (±)-cis-2,3-dihydro-3-[(3,4-dihydroxybenzoyl)oxy]-5-[2-(dimethylamino)ethyl]-2-(4-methoxyphenyl)naphtho[1,2-b][1,4]thiazepin-4(5H)-one hydrochloride semihydrate, mp 198°–199°.

$C_{31}H_{30}N_2O_6S \cdot HCl \cdot 0.5H_2O$ (603.07): Calcd: C, 61.74; H, 5.35; N, 4.64. Found: C, 61.87; H, 5.39; N, 5.07.

EXAMPLE 9

(±)-cis-2,3-Dihydro-2-(4-methoxyphenyl)-3-[(3,4,5-trimethoxybenzoyl)oxy]-5-[2-(dimethylamino)ethyl]-naphtho[1,2-b][1,4]thiazepin-4(5H)-one To a solution of 1.50 g (0.0035 mol) of (±)-cis-2,3-dihydro-3-hydroxy-2-(4-methoxyphenyl)-5-[2-(dimethylamino)ethyl]naphtho[1,2-b][1,4]thiazepin-4(5H)-one, in 20 ml of dry pyridine was added dropwise 1.4 g (0.0059 mol) of 3,4,5-trimethoxybenzoyl chloride at ice-bath temperature. The mixture was stirred at this temperature for 17 hours and concentrated to dryness. The residue was partitioned between methylene chloride and dilute ammonium hydroxide. The methylene chloride extracts were washed with brine and dried ($MgSO_4$). Removal of the solvent gave a residue, which was dissolved in a mixture of acetone-methylene chloride (70:30) and chromatographed on 40 g silica gel. The column was eluted with 50 ml portions of acetone-methylene chloride (70:30). Fractions 4–15 were combined and the solvent was removed under reduced pressure to give 1.3 g of crude product, which after crystallization from ethanol afforded 1.2 g (55%) of (±)-cis-2,3-dihydro-2-(4-methoxyphenyl)-3-[(3,4,5-trimethoxybenzoyl)oxy]-5-[2-(dimethylamino)ethyl]naphtho[1,2-b][1,4]thiazepin-4(5H)-one, mp 189°–190°.

$C_{34}H_{36}N_2O_7S$ (616.44); Calcd: C, 66.22; H, 5.88; N, 4.54. Found: C, 66.22; H, 5.77; N, 4.69.

The above base, 1.2 g (0.0019 mol) was dissolved in acetone and acidified with hydrogen chloride (anhydrous) to give 1.0 g (78%) of (±)-cis-2,3-dihydro-2-(4-methoxyphenyl)-3-[(3,4,5-trimethoxybenzoyl)oxy]-5-[2-(dimethylamino)ethyl]naphtho[1,2-b][1,4]thiazepin-4(5H)-one hydrochloride as the semihydrate, mp 255°–256°.

$C_{34}H_{36}N_2O_7S \cdot HCl \cdot 0.5H_2O$ (662.14); Calcd: C, 61.56; H, 5.78; N, 4.20; Found: C, 61.22; H, 5.70; N, 4.17;

EXAMPLE 10

±)-cis-2,3-Dihydro-3-[4-[[[4-hydroxy-3,5-bis(1,1-dimethylethyl)benzoyl]oxy]bis-3,5-(1,1-dimethylethyl)benzoyl]oxy]-5-[2-(dimethylamino)ethyl]-2-(4-methoxyphenyl)naphtho[1,2-b][1,4]thiazepin-4(5H)-one To a solution of 1.5 g (0.0035 mol) of (±)-cis-2,3-dihydro-3-hydroxy-2-(4-methoxyphenyl)-5-[2-(dimethylamino)ethyl]naphtho[1,2-b][1,4]thiazepin-4(5H)-one in 20 ml of dry pyridine (dried over KOH) was added dropwise 1.6 g (0.0059 mol) of 3.5 di-tert-butyl-4-hydroxybenzoyl chloride at ice-bath temperature. The mixture was stirred at this temperature for 17 hours and concentrated to dryness. The residue was partitioned between ethyl acetate and dilute ammonium hydroxide. The combined ethyl acetate solutions were washed with brine and dried ($MgSO_4$). Removal of the solvent gave a residue, which was dissolved in chloroform and chromatographed on 40 g of silica gel. The column was eluted with 50 ml portions of chloroform-acetone (90:10). Fractions and 14 and 15 were combined and the solvents were removed to give 0.9 g (29%) (±)-cis-2,3-dihydro-3-[4-[[[4-hydroxy-3,5-bis(1,1-dimethylethyl)benzoyl]oxy]bis-3,5-(1,1-dimethylethyl)benzoyl]oxy]-5-[2-(diethylamino)ethyl]-2-(4-methoxyphenyl)naphtho[1,2-b][1,4]thiazepin-4(5H)-one, as an amorphous solid.

$C_{54}H_{66}N_2O_7S$ (887.18); Calcd: C, 73.10; H, 7.51; N, 3.16. Found: C, 73.56; H, 7.88; H, 2.95.

The above base, 0.9 g (0.001 mol) in acetonitrile was treated with 0.11 g (0.001 mol) of fumaric acid. The resulting crystals were collected to afford 0.4 g (42,) of (±)-cis-2,3-dihydro-3-[4-[[[4-hydroxy-3,5-bix-(1,1-dimethylethyl)benzoyl]oxy]-bis-3,5-(1,1-dimethylethyl)benzoyl]oxy]-5-[2-(dimethylamino)ethyl]-2-(4-methoxyphenyl)naphtho[1,2-b][1,4]thiazepin-4(5H)-one (E)-2-butenedioate, mp 170°–172°.

$(C_{54}H_{66}N_2O_7S)_2.C_4H_4O_4$ (945.22); Calcd: C, 68.64; H, 6.99; N, 2.96. Found: C, 68.67; H, 7.06; N, 2.76.

EXAMPLE 11

(+)-cis-2,3-Dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one.

To a solution of 1.5 g (0.0035 mol) of (+)-cis-2,3-dihydro-3-hydroxy-2-(4-methoxyphenyl)-5-[2-(dimethylamino)ethyl]naphtho[1,2-b][1,4]thiazepin-4(SH)-one in 20 ml of dry pyridine (dried over KOH) was added dropwise 1.2 g (0.0059 mol) of 3,4-dimethoxybenzoyl chloride at ice-bath temperature. The mixture was kept at this temperture for 17 hours and concentrated to dryness. The residue was partitioned between ethyl acetate and cold dilute ammonium hydroxide. The combined ethyl acetate solutions were washed with brine, dried (MgSO4) and the solvent was removed. The residue was dissolved in acetonitrile and chromatographed using 40 g of silica gel. The column was eluted with 50 ml portions of a mixture of acetonitrile-acetone (70:30). Fractions 9–16 were combined and the solvents were removed to give 1.9 g (90%) of amorphous (+)-cis-2,3-dihydro-3-[(3,4-dimethoxybenzoyl)oxy]-2-(4-methoxyphenyl)-5-[2-(dimethylamino)ethyl]naphtho[1,2-b]1,4thiazepin-4-(5H)-one as an amorphous semihydrate, $[\alpha]_D^{25} -47.62°$ (C 0.949, MeOH).

$C_{33}H_{34}N_2O_6S.0.5H_2O$ (595.71); Calcd: C, 66.53; H, 5.92; N, 4.70. Found: C, 67.01; H, 5.94; N, 4.83;

The above base, 1.9 g (0.0032 mol), was dissolved in ethanol and 1.4 g (0.0032 mol) of fumaric acid added. The resulting crystals were collected to afford 1.6 g (39%) of (+)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one (E)-2-butenedioate hydrate, mp 134°–135°, $[\alpha]_D^{25} -37.9°$ (C 1.01, MeOH)

$(C_{33}H_{34}N_2O_6S)_2.C_4H_4O_4.H_2O$ (1307.43); Calcd: C, 64.30; H, 5.71; N, 4.28. Found: C, 64.57; H, 5.52; N, 4.26.

EXAMPLE 12

(+)-cis-[2R-[2R*(4R*,8R*)]]-Butanedioic acid 3,4-dihydro-2,5,7,8-tetramethyl-2-(4,8,12-trimethyltridecyl)-2H-1-benzopyran-6-yl-2,3,4,5-tetrahydro-3-hydroxy-2-(4-methoxyphenyl)-5-[2-(dimethylamino)ethyl]-4-oxonaphtho[1,2-b][1,4]thiazepin-3-yl ester To a solution of 2.0 g (0.0047 mol) of (+)-cis-2,3-dihydro-3-hydroxy-2-(4-methoxyphenyl)-5-[2-(dimethylamino)ethyl]naphtho[1,2-b][1,4]thiazepin-4-(5H)-one in 25 ml of pyridine (dried over KOH) was added dropwise a solution of 5.0 g (0.009 mol) of d-α-tocopherol succinyl chloride in 5 ml methylene chloride over a period of 5 minutes at ice-bath temperature and the mixture was kept at this temperature for 17 hours. The mixture was concentrated and the residue was partitioned between ethyl acetate and dilute ammonium hydroxide. The combined ethyl acetate solutions were washed with brine, dried (MgSO4) and concentrated. The residue was dissolved in acetone and chromatographed on 75 g silica gel. The column was eluted with acetone. Fractions 5–9 were combined and the solvent was removed under reduced pressure to give 3.5 g (79%) of (+)-cis-[2R-[2R*(4R*,8R*)]]-butanedioic acid 3,4-dihydro-2,5,7,8-tetramethyl-2-(4,8,12-trimethylt ridecyl)-2H-1-benzopyran-6-yl-2,3,4,5-tetrahydro-3-hydroxy-2-(4-methoxyphenyl)-5-[2-(dimethylamino)ethyl]-4-oxonaphtho[1,2-b][1,4]thiazepin-3-yl ester as an amorphous solid, $[\alpha]_D^{25} -14.28°$ (C 0.49, MeOH).

$C_{57}H_{78}N_2O_7S$ (935.18); Calcd: C, 73.00; H, 8.33; N, 3.04. Found: C, 72.96; H, 8.32; N, 2.99.

The above base, 1.7 g (0.0018 mol) in ether was treated with 0.21 g (0.0018 mol) of fumaric acid. The resulting crystals were separated to afford 1.5 g (79%) of (+)-cis-[2R-[2R*[4R*, 8R*)]]-butanedioic acid 3,4-dihydro-2,5,7,8-tetramethyl-2-(4,8,12-trimethyltri decyl)-2H-1-benzopyran-6-yl-2,3,4,5-tetrahydro-3-hydroxy-2-(4-methoxyphenyl)-5-[2-(dimethylamino)ethyl]-4-oxonaphtho[1,2-b][1,4]thiazepin-3-yl ester (E)-2-butenedioate 0.25 molar hydrate, mp 98°–99°, $[\alpha]_D^{25} -15.23°$ (C 0.459, MeOH).

$C_{57}H_{78}N_2O_7S.C_4H_4O_4.0.25 H_2O$ (1055.75); Calcd: C, 69.39; H, 7.84; N, 2.65; H2O, 0.42. Found: C, 69.63; H, 7.97; N, 2.66; H2O, 0.61.

EXAMPLE 13

(−)-cis-2,3-Dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one.

To a solution of 2.0 g (0.0047 mol) of (−)-cis-2,3-dihydro-3-hydroxy-2-(4-methoxyphenyl)-5-[2-(dimethylamino)ethyl]naphtho[ 1,2-b][1,4]thiazepin-4(5H)-one in 25 ml of dry pyridine was added dropwise 1.6 g (0.0082 mol) of 3,4-dimethoxybenzoyl chloride at ice-bath temperature. After the addition, the reaction mixture was kept at ice-bath temperatures for 17 hours and then concentrated under reduced pressure. The residue was partitioned between ethyl acetate and cold 10% potassium carbonate. The combined ethyl acetate solutions were washed with brine, dried (MgSO4) and the solvent was removed to give 3.3 g of crude product, which was dissolved in methylene chloride and chromatographed using 45 g of silica gel. The comumn was eluted with 50 ml portions of methylene chloride-acetone (80:20). Fractions 21–50 were collected and the solvent was removed to give 2.5 g (92%) of (−)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one as an amorphous solid, $[\alpha]_D^{25} +47.39°$ (C 0.928, MeOH).

$C_{33}H_{34}N_2O_6S$ (586.68); Calcd: C, 67.56; H, 5.84; N, 4.78. Found: C, 67.19; H, 5.88; N, 4.76.

To the above base, 2.5 g (0.0043 mol), in acetone was combined with 0.5 g (0.0043 mol) of fumaric acid. The crystals were separated to give 1.9 g (34%) of (−)-cis-2,3-dihydro-3-[(3,4-dimethoxybenzoyl)oxy]-2-(4-methoxyphenyl)-5-[2-(dimethylamino)ethyl]naphtho(1,2-b][1,4]thiazepin-4(5H)-one (E)-2-butenedioate as the hydrate, mp 135°–136°, [α]$_D^{25}$+39.8° (C 1.00, MeOH).

(C$_{33}$H$_{34}$N$_2$O$_6$S)$_2$.C$_4$H$_4$O$_4$.H$_2$O (1307.43); Calcd: C, 64.30; H, 5.71; N, 4.28. Found: C, 64.48; H, 5.77; N, 4.34.

EXAMPLE 14

(±)-cis-2,3-Dihydro-3-[[4-hydroxy-3,5-bis(1,1-dimethylethyl)benzoyl]oxy]-2-(4-methoxyphenyl)-5-[2-(dimethylamino)ethyl]naphtho[1,2-b][1,4]thiazepin-4(5H)-one A mixture of 1.35 g (0.00054 mol) of 3,5-di-tert.-butyl-4-hydroxybenzoic acid and 0.9 g (0.0054 mol) of 1,1'-carbonyldiimidazole in 20 ml of dry tetrahydrofuran was stirred at room temperature for 30 minutes. To the above mixture 1.3 g (0.00031 mol) of (±)-cis-2,3-dihydro-3-hydroxy-2-(4-methoxyphenyl)-5-[2-(dimethylamino)ethyl]naphtho[1,2-b][1,4]thiazepin-4(5H)-one was added and stirred at room temperature for 17 hours then at reflux for 7 hours. After cooling the solids were filtered and the filtrate was concentrated to dryness. The residue was partitioned between ethyl acetate and dilute ammonium hydroxide. The ethyl acetate solutions were washed with brine, dried (MgSO$_4$) and the solvent was removed under reduced pressure. The residue was dissolved in acetonitrile and chromatographed on 45 g of silica gel. The column was eluted wtih 50 ml portions of acetonitrile. Fractions 10–20 were combined and the solvent was removed to give 0.9 g of crude product, which was crystallized from ether to give 0.8 g (40%) of (±)-cis-2,3-dihydro-3-[[4-hydroxy-3,5-bis(1,1-dimethylethyl)benzoyl]oxy]-2-(4-methoxyphenyl)-5-[2-dimethylamino)ethyl]naphtho[1,2-b][1,4]thiazepin-4(5H)-one, mp 181°–182°.

C$_{39}$H$_{46}$N$_2$O$_5$S (654.77); Calcd: C, 71.54; H, 7.08; N, 4.28. Found: C, 71.23; H, 7.16; N, 4.22.

A sample of the above base, on treatment with hydrogen chloride (anhydrous) in acetone, afforded (±)-cis-2,3-dihydro-3-[[4-hydroxy-3,5-bis(1,1-dimethylethyl)benzoyl]oxy]-2-(4-methoxyphenyl)-5-[2-dimethylamino)ethyl[naphtho[1,2-b][1,4]thiazepin-4(5H)-one hydrochloride as the hydrate, mp 229°–230°.

C$_{39}$H$_{46}$N$_2$O$_5$S.HCl .H$_2$O (709.34); Calcd: C, 66.04; H, 6.96; N, 3.95. Found: C, 66.30; H, 7.02; N, 3.91.

EXAMPLE 15

[±)-cis-3(2alpha or 2beta)]-2,3-Dihydro-3-[[[3,4-dihydro-6-hydroxy-2-methyl-5,7-bis(1-methylethyl)-2H-1-benzopyran-2-yl]carbonyl]-5-[2-(dimethylamino)ethyl]-2-(4-methoxyphenyl)naphtho[1,2-b][1,4]thiazepin-4(5H)-one (Isomers "A" and "B")

After a solution of 1.4 g (0.0048 mol) of (±)-5,7-diisopropyl-6-hydroxy-2-methylchroman-2-carboxylic acid and 0.9 g (0.0055 mol) of 1,1'-carbonyldiimidazole in 25 ml of dry tetrahydrofuran was stirred at room temperature for 1 hour, 2.0 g (0.0047 mol) of (±)-cis-2,3-dihydro-3-3-hydroxy-2-(4-methoxyphenyl)-5-[2-(dimethylamino)ethyl]naphtho[1,2-b][1,4]thiazepin-4(5H)-one and 20 mg of 4-dimethylaminopyridine were added. The mixture was stirred at room temperature for 48 hours, then concentrated under reduced pressure and the residue was partitioned between ethyl acetate and cold dilute ammonium hydroxide. The combined ethyl acetate solutions were washed with brine, dried (MgSO$_4$) and the solvent was removed under reduced pressure. The residue was dissolved in acetonitrile and chromatographed on 80 g of silica gel. The column was eluted with 75 ml portions of acetonitrile. Fractions 6–9 were combined and the solvent was removed to give 0.8 g (24%) of isomer "A" as an amorphous solid.

C$_{41}$H$_{48}$N$_2$O$_6$S (696.81); Calcd: C, 70.67; H, 6.94; N, 4.02. Found: C, 70.47; H, 7.06; N, 3.92.

The above base, 0.8 g (0.0011 mol), was combined with 0.13 g (0.0011 mol) of fumaric acid in acetone. The resulting crystals were collected to afford 0.5 g (54%) of the (E)-2-butenedioate, of isomer "A", mp 128°–130°.

C$_{41}$H$_{48}$N$_2$O$_6$S.C$_4$H$_4$O$_4$ (812.94): Calcd: C, 66.48; H, 6.46; N, 3.44. Found: C, 66.02; H, 6.39; N, 3.47.

Chromatographic separation of the above reaction mixture was continued and fractions 13–26 were combined. After removal of the solvent the second isomer to elute was crystallized from ethyl ether to afford 1.1 g (33%) of isomer "B", mp 219°–220°.

C$_{41}$H$_{48}$N$_2$O$_6$S (696.81); Calcd: C, 70.67; H, 6,94; N, 4.02. Found: C, 70.55; H, 7.03; N, 4.03.

The above base, 1.1 g (0.0016 mol), was dissolved in acetone and acidified with hydrogen chloride (anhydrous). The resulting crystals were separated to afford 0.8 g (69%) of the hydrochloride, of isomer "B", mp 184°–185°.

C$_{41}$H$_{48}$N$_2$O$_6$S.HCl (733.26); Calcd: C, 67.15; H, 6.73; N, 3.82. Found: C, 66.72; H, 6.82; N, 3.76.

EXAMPLE 16

(±)-cis-2,3-Dihydro-2-(4-methoxyphenyl)-5-[2-(dimethylamino)ethyl]-3-[(3-pridinylcarbonyl)oxy]naphtho[1,2-b][1,4]thiazepin-4(5H)-one A mixture of 0.5 g (0.004 mol) of nicotinic acid and 0.7 g (0.004 mol) of 1,1'-carbonyldiimidazole in 20 ml of dry tetrahydrofuran was stirred at room temperature for 1 hour. To the solution was added 1.3 g (0.003 mol) of (±)-cis-2,3-dihydro-3-hydroxy-2-(4-methoxyphenyl)-5-(2-(dimethylamino)ethyl]naphtho[1,2-b][1,4]thiazepin-4(5H)-one and the reaction mixture was stirred at room temperature for 17 hours. After concentrating to dryness the residue was partitioned between ethyl acetate and dilute ammonium hydroxide. The ethyl acetate solutions were washed with brine and dried (MgSO$_4$). Removal of the solvent at reduced pressure gave 2.2 g of crude base which was dissolved in acetone and acidified with hydrogen chloride (anhydrous). The resulting crystals were separated to afford 1.9 g (99%) of (±)-cis-2,3-dihydro-2-(4-methoxyphenyl)-5-[2-(dimethylamino)ethyl]-3-[(3-pyridinylcarbonyl)oxy]naphtho[1,2-b][1,4]thiazepin-4(4H)-one dihydrochloride (4:5) hydrate, mp 178°–179°.

C$_{30}$H$_{29}$N$_3$O$_4$S.2HCl.4:5 H$_2$O (622.52); Calcd: C, 57.87; H, 5.34; N, 6.74; H$_2$O.61. Found: C, 57.52; H, 5.28; N, 6.49; H$_2$O 3.61.

The above dihydrochloride, 1.9 g (0.003 mol), was dissolved in water, basified with dilute ammonium hydroxide and extracted with ethyl acetate. The combined organic solutions were washed with brine, dried (MgSO$_4$) and the solvent was removed to give 1.6 g of crude product. This compound was crystallized from ether to afford 1.4 g (87%) of (±)-cis-2,3-dihydro-2-(4-methoxyphenyl)-5-[2-(dimethylamino)ethyl]-3-[(3-pyridinylcarbonyl)oxy] naphtho[1,2-b][1,4]thiazepin-4(5H)-one, mp 144°–145°.

C$_{30}$H$_{29}$N$_3$O$_4$S (527.62); Calcd: C, 68.30; H, 5.54; N, 7.97. Found: C, 68.26; H, 5.65; N, 7.96.

EXAMPLE 17

(+)-cis-[3(2alpha or 2beta)]-2,3-Dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one (Isomers "A" and "B")

To a solution of 1.4 g (0.0048 mol) of (±)-5,7-diisopropyl-6-hydroxy-2-methylchroman-2-carboxylic acid in 25 ml dry tetrahydrofuran was added 0.09 g (0.0055 mol) of 1,1'-carbonyldiimidazol. After stirring at room temperature for 30 minutes, 2.0 g (0.0047 mol) (±)-cis-2,3-dihydro-3-hydroxy-2-(4-methoxyphenyl)-5-[2-(dimethylamino)ethyl]naphtho[1,2-b][1,4]thiazepin-4(5H)-one and 20 mg of 4-dimethylaminopyridine were added. The reaction mixture was stirred at room temperature for 17 hours, concentrated to dryness and the residue was partitioned between ethyl acetate and dilute ammonium hydroxide. The combined ethyl acetate solutions were washed with brine, dried (MgSO4) and the solvent was removed under reduced pressure. The residue was dissolved in acetonitrile and chromatographed on 70 g silica gel. The column was eluted with 75 ml portions of acetonitrile. Fractions 5–8 were combined and the solvent removed to give 1.3 g (40%) of isomer "A" as an amorphous solid, $[\alpha]_D^{25} -74.31°$ (C 1.03, MeOH).

$C_{41}H_{48}N_2O_6S$ (696.81); Calcd: C, 70.67; H, 6.94; N, 4.02. Found: C, 70.32; H, 6.95; N, 3.98.

The above base, 1.3 g (0.0019 mol), in acetone was treated with 0.215 g (0.0019 mol) of fumaric acid. The crystals were separated to afford 1.0 g (65%) of the (E)-2-butenedioate monohydrate, of isomer "A", mp 150°–151°, $[\alpha]_D^{25} -58.52°$ (C 0.972, MeOH).

$C_{41}H_{48}N_2O_6S.C_4H_4O_4.H_2O$ (830.94); Calcd: C, 65.04; H, 6.56; N, 3.36. Found: C, 64.96; H, 6.21; N, 3.25.

Chromatographic separation of the above reaction mixture was continued and fractions 12–22 were combined and the solvent was removed under reduced pressure. The second isomer was crystallized from ether to afford 1.0 g (31%), of isomer "B", mp 200°–201°, $[\alpha]_D^{25} -75.67°$ (C 0.91, MeOH).

$C_{41}H_{48}N_2O_6S$ (696.81); Calcd: C, 70.67; H, 6.94; N, 4.02. Found: C, 70.50; H, 6.63; N, 3.92.

The above base, 1.0 g (0.0014 mol), in acetone was treated with 0.17 g (0.0014 mol) of fumaric acid. The crystals were separated to afford 1.0 g (86%) of the (E)-2-butenedioate, of isomer "B", mp 134°–136°, $[\alpha]_D^{25} -64.67°$ (C 1.00, MeOH).

$C_{41}H_{48}N_2O_6S.C_4H_4O_4$ (812.95); Calcd: C, 66.48; H, 6.46; N, 3.44. Found: C, 66.20; H, 6.46; N, 3.45.

EXAMPLE 18

[(+)-cis-3(2alpha and 2beta)1-2,3-Dihydro-3-[[(3,4-dihydro-6-hydroxy-2,5,7,8-tetramethyl-2H-1-benzopyran-2-yl)carbonyl]oxy]-2-(4-methoxyphenyl)-5-[2-(dimethylamino)ethyl]naphtho[1,2-b][1,4]thiazepin-4(5H)-one To a solution of 1.2 g (0.0048 mol) of (±)-6-hydroxy-2,5,7,8-tetramethylchroman-2-carboxylic acid in 25 ml of dry tetrahydrofuran was added 0.9 g (0.0055 mol) of 1,1'-carbonyldiimidazole. After stirring for 30 minutes at room temperature, 2.0 g (0.0047 mol) of (±)-cis-2,3-dihydro-3-hydroxy-2-(4-methoxyphenyl)-5-[2-(dimethylamino)ethyl]naphtho[1,2-b][1,4]thiazepin-4(5H)-one and 20 mg of 4-dimethylaminopyridine were added and the reaction mixture was stirred at room temperature for 17 hours. The mixture was concentrated and the residue in water, was made basic with concentrated ammonium hydroxide. The aqueous suspension was extracted with ethyl acetate (3×60 ml). The combined ethyl acetate solutions were washed with brine and dried (MgSO4). Removal of the solvent gave the crude product which was chromatographed on 40 g silica gel and the column was eluted with 20 ml fractions of ethyl acetate. Fractions 4–25 were combined and the solvent was removed to give 1.5 g (48%) of amorphous [(+)-cis-3(2alpha and 2beta)]-2,3-di-hydro-3-[[(3,4-dihydro-6-hydroxy-2,5,7,8-tetramethyl-2H-1-benzo-pyran-2-yl)carbonyl]oxy]-2-(4-methoxyphenyl)-5-[2-(dimethylamino)ethyl]naphtho[1,2-b][1,4]thiazepin-4(5H)-one semihydrate (1:1 diastereomer by NMR), $[\alpha]_D^{25} -49.46°$ (C 0.972, MeOH).

$C_{38}H_{42}N_2O_6S.0.5\ H_2O$ (663.73); Calcd: C, 68.75; H, 6.54; N, 4.22. Found: C, 68.64; H, 6.54; N, 4.20.

The above base, 1.5 g (0.0023 mol) on treatment with hydrogen chloride (anhydrous) in ethyl acetate afforded 1.2 g (75%) of [(+)-cis-3(2alpha and 2beta)]-2,3-dihydro-3-[[(3,4-dihydro-6-hydroxy-2,5,7,8-tetramethyl-2H-1-benzopyran-2-yl)carbonyl]oxy]-2-(4-methoxyphenyl)-5-[2-(dimethylamino)ethyl]naphtho[1,2-b][1,4]thiazepin-4(5H)-one hydrochloride hydrate, mp 240°–241°, $[\alpha]_D^{25} -72.05°$ (C 0.411, MeOH).

$C_{38}H_{42}N_2O_6S.HCl.H_2O$ (709.23); Calcd: C, 64.65; H, 6.40; N, 3.95. Found: C, 64.94; H, 6.28; N, 4.09.

EXAMPLE 19

(+)-cis-2,3-Dihydro-3-[[(tetrahydro-2,2,5,5-tetramethyl-7H-dioxolo[4,5]furo[3,2-d][1,3]dioxin-3a-yl)carbonyl]oxy]-2-(4-methoxyphenyl)-5-[2-(dimethylamino)ethyl]naphtho[1,2-b][1,4]thiazepin-4(5H)-one.

To a solution of 1.3 g (0.0048 mol) of (−)-diacetone-2-keto-L-gulonic acid in 20 ml tetrahydrofuran was added 0.9 g (0.0055 mol) of 1,1'-carbonyldiimidazole. After stirring for 30 minutes at room temperature, 2.0 g (0.0047 mol) of (+)-cis-2,3-dihydro-2-hydroxy-2-(4-methoxyphenyl)-5-[2-(dimethylamino)ethyl]naphtho[1,2-b][1,4]thiazepin-4(5H)-one and 40 mg of 4-dimethylaminopyridine were added and stirred at room temperature for 17 hours. The mixture was concentrated and the residue in water was made basic with concentrated ammonium hydroxide. The aqueous suspension was extracted with ethyl acetate (3×60 ml). The combined ethyl acetate solutions were washed with brine and dried (MgSO4). Removal of solvent gave the crude product, which after crystallization from ethyl acetate afforded 1.4 g (44%) of (+)-cis-2,3-dihydro-3-[[(tetrahydro-2,2,5,5-tetramethyl-7H-dioxolo[4,5]furo[3,2-d][1,3]dioxin-3a-yl)carbonyl]oxy]-2-(4-methoxyphenyl)-5-[2-(dimethylamino)ethyl]naphtho[1,2-b][1,4]thiazepin-4(5H)-one, mp 220°–221°, $[\alpha]_D^{25} -17.28°$ (C 0.52, MeOH).

$C_{36}H_{42}O_9S$ (678.77); Calcd: C, 63.70; H, 6.25; N, 4.13. Found: C, 63.38; H, 6.17; N, 4.29.

The above base, 1.2 g (0.0018 mol) was dissolved in 15 ml of acetone and treated with 0.208 g (0.0018 mol) of fumaric acid. The crystals were separated to give 1.9 g (77%) of (+)-cis-2,3-dihydro-3-[[(tetrahydro-2,2,5,5-tetramethyl-7H-dioxolo[4,5]furo[3,2-d][1,3]dioxin-3a-yl)carbonyl]oxy]-2-(4-methoxyphenyl)-5-[2-(dimethylamino)ethyl]naphtho[1,2- b][1,4]thiazepin-4(5H)-one (E)-2-butenedioate semihydrate, mp 190°–191°, $[\alpha]_D^{25} -27.89°$ (C 0.49, MeOH).

$C_{36}H_{42}N_2O_9S \cdot C_4H_4O_4 \cdot 0.5\ H_2O$ (803.84); Calcd: C, 59.76; H, 5.77; N, 3.48. Found: C, 59.83; H, 5.69; N, 3.61.

EXAMPLE 20

Tablets

| Item | Ingredient | mg/tablet 100 mg | mg/tablet 200 mg |
|---|---|---|---|
| 1. | (+)-cis-2,3-dihydro-3-[(3,4-dimethoxybenzoyl)oxy]-2-(4-methoxyphenyl)-5-[2-(dimethylamino)ethyl]-naphtho[1,2-b][1,4]thiazepin-4(5H)-one hydrochloride | 100 | 200 |
| 2. | Lactose | 100 | 200 |
| 3. | Polyvinylpyrrolidone(PVP) | 10 | 20 |
| 4. | Modified Starch | 10 | 20 |
| 5. | Magnesium Stearate | 3 | 6 |
|  |  | 223 mg | 446 mg |

(1) Mix items 1, 2 and 4 and granulate with PVP in water or alcohol.
(2) Dry the granulation at 45° C.
(3) Mill the dried granulation through a suitable mill.
(4) Add Item 5 and mix for three minutes and compress on a suitable press.

EXAMPLE 21

Capsules

| Item | Ingredient | mg/capsule 100 mg | mg/capsule 200 mg |
|---|---|---|---|
| 1. | (+)-cis-2,3-Dihydro-3-[(3,4-dimethoxybenzoyl)oxy]-2-(4-methoxyphenyl)-5-[2-(dimethylamino)ethyl]-naphtho[1,2-b][1,4]thiazepin-4(5H)-one hydrochloride | 100 | 200 |
| 2. | Corn Starch (Pregelatinized) | 50 | 80 |
| 3. | Modified Starch | 10 | 20 |
| 4. | Talc | 20 | 20 |
| 5. | Magnesium Stearate | 1 | 1 |
|  |  | 181 mg | 322 mg |

(1) Mix Items 1–3 and wet granulate with water. Dry at 45° C. overnight.
(2) Mill through suitable screen using appropriate milling equipment.
(3) Add Items 4 and 5 and mix for five miniutes.
(4) Fill into suitable capsule.

EXAMPLE 22

Parenteral Solution

| Item | Ingredient | mg/ml |
|---|---|---|
| 1. | (+)-cis-2,3-dihydro-3-[(3,4-dimethyloxybenzoyl)oxy]-2-(4-methoxyphenyl)-5-[2-(dimethylamino)ethyl]naphtho[1,2-b][1,4]thiazepin-4(5H)-one hydrochloride | 10 |
| 2. | Benzyl Alcohol | 10 |
| 3. | Sorbitol | 38 |
| 4. | Hydrochloric Acid q.s. to pH | 3–7 |
| 5. | Sodium Hydroxide q.s. to pH | 3–7 |
| 6. | Water for Injection q.s. to | 1 ml |

In the above parenteral solution q.s. means sufficient quantity.

We claim:

1. A (+)-cis compound of the formula

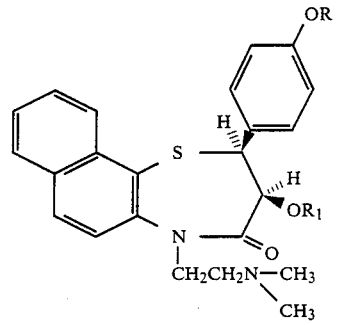

wherein R is lower alkyl; $R_1$ is

wherein $R_3$ is pyridyl,

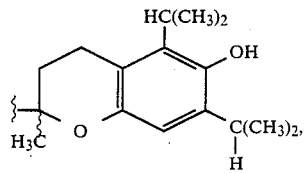

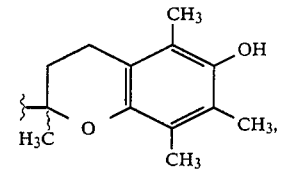

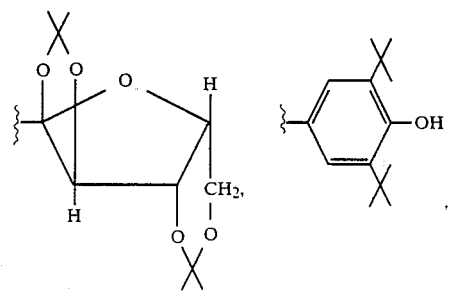

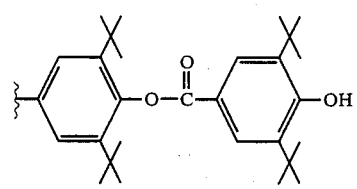

-continued

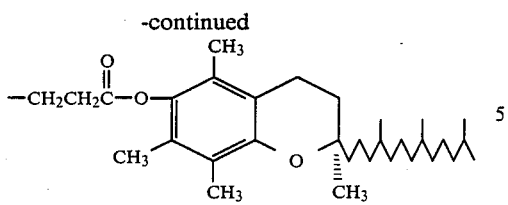

or phenyl unsubstituted or substituted by up to 3 substituents selected from the group consisting of hydroxy, halogen, lower alkoxy, and lower alkanoyloxy;
a (−)cis enantiomer, or a (±)-cis racemate thereof; or a pharmaceutically acceptable acid addition salt thereof.

2. A (+)-cis compound in accordance with claim 1, of the formula

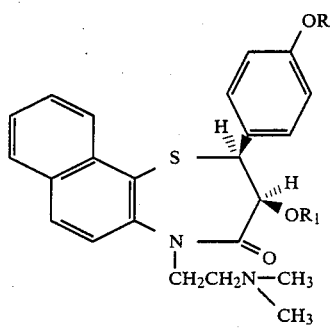

wherein R is lower alkyl; $R_1$ is

wherein $R_3$ is pyridyl,

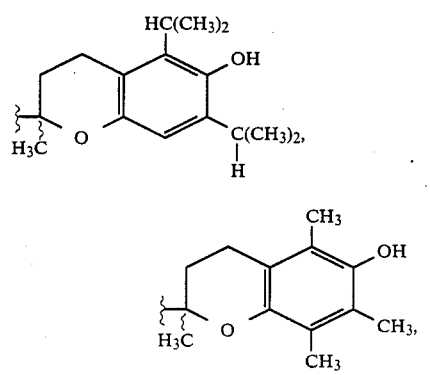

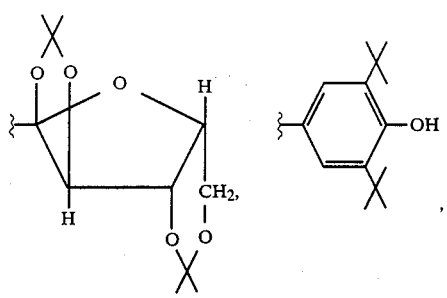

-continued

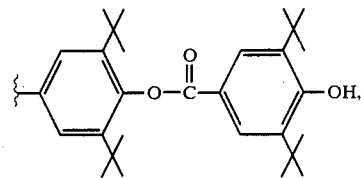

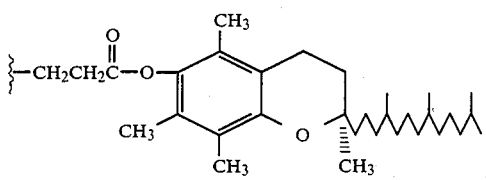

or phenyl unsubstituted or substituted by up to 3 substituents selected from the group consisting of hydroxy, halogen, lower alkoxy, and lower alkanoyloxy;
or a pharmaceutically acceptable acid addition salt thereof.

3. A compound in accordance with claim 2, wherein R is methyl.

4. A compound in accordance with claim 3, whreein $R_1$ is

wherein $R_3$ is phenyl unsubstituted or substituted by up to 3 substituents selected from the group consisting of hydroxy, halogen, lower alkoxy, and lower alkanoyloxy.

5. A compound in accordance with claim 4, wherein $R_3$ is phenyl substituted by 1 to 3 methoxy groups.

6. The compound in accordance with claim 5, (+)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one, the semihydrate thereof or the (E)-2-butenedioate hydrate thereof.

7. A compound in accordance with claim 3, wherein $R_3$ is

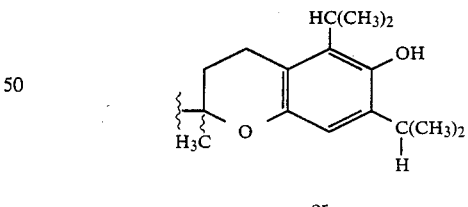

or

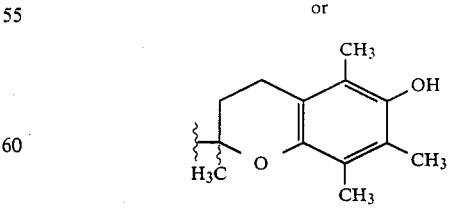

8. The compound in accordance with claim 7, [(+)-cis-3(2α or 2β)]-2,3-dihydro-3-[[[3,4-dihydro-6-hydroxy-2-methyl-5,7-bis(1-methylethyl)-2H-1-benzopyran-2-yl]carbonyl]oxy]-5-[2-dimethylamino)ethyl]-2-(4-methoxyphenyl)naphtho[1,2-b][1,4]thiazepin- 4(5H)-one; or the (E)-2-butenedioate salt thereof (Isomer "B").

9. The compound in accordance with claim 7, [(+)-cis-3(2α or 2β)[-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one, or the (E)-2-butenedioate salt thereof (Isomeer "A".)

10. The compound in accordance with claim 7, [(+)-cis-[3(2α and 2β)]-2,3-dihydro-3-[[(3,4-dihydro-6-hydroxy-2,5,7,8-tetramethyl-2H-1-benzopyran-2-yl)carbonyl]oxy]-2-(4-methoxyphenyl)-5-[2-(dimethylamino)ethyl]naphtho[1,2-b][1,4]thiazepin-4(5H)-one, the semihydrate thereof, or the hydrochloride hydrate thereof.

11. The compound in accordance with claim 3, (+)-cis-2,3-dihydro-3-[[(tetrahydro-2,2,5,5-tetramethyl-7H-dioxolo[4,5]furo[3,2-d][1,3]dioxin-3a-yl)carbonyl]oxy]-2-(4-methoxyphenyl)-5-[2-(dimethylamino)ethyl]naphtho[1,2-b][1,4]thiazepin-4(5H)-one, or the (E)-2-butenedioate semihydrate thereof.

12. The compound in accordance with claim 3, (+)-cis-[2R-[2R*(4R*,8R*)]-butanedioic acid 3,4-dihydro-2,5,7,8-tetramethyl-2-(4,8,12-trimethyltridecyl)-2H-1-benzopyran-6-yl-2,3,4,5-tetrahydro-3-hydroxy-2-(4-methoxyphenyl)-5-[2-(dimethylamino)ethyl]-4-oxonaphtho[1,2-b][1,4]thiazepin-3-yl ester, or the (E)-2-butenedioate salt thereof.

13. A compound in accordance with claim 1, wherein R is methyl.

14. A compound in accordance with claim 13, wherein $R_1$ is

wherein $R_3$ is phenyl unsubstituted or substituted by up to 3 substituents selected from the group consisting of nitro, hydroxy, halogen, lower alkoxy, and lower alkanoyloxy.

15. A compound in accordance with claim 14, wherein $R_3$ is phenyl substituted by 1 to 3 methoxy groups.

16. The compound in accordance with claim 15, (±)-cis-3-[(3,4-dimethoxybenzoyl)oxy]-2,3-dihydro-5-[2-(dimethylamino)ethyl]-2-(4-methoxyphenyl)naphtho[1,2-b][1,4]thiazepin-4(5H)-one, or the hydrochloride semihydrate salt thereof.

17. The compound in accordance with claim 15, (−)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one, or the (E)-2-butenedioate salt thereof.

18. The compound in accordance with claim 15, (±)-cis-2,3-dihydro-2-(4-methoxyphenyl)-3-[(3,4,5-trimethoxybenzoyl)oxy]-5-[2-dimethylamino)ethyl]-naphtho[1,2-b][1,4]thiazepin-4(5H)-one, or the hydrochloride semihydrate salt thereof.

19. A compound in accordance with claim 14, wherein $R_3$ is phenyl substituted by 1 or 2 acetyloxy groups.

20. The compound in accordance with claim 19, (±)-cis-3-[[(2-acetyloxy)benzoyl]oxy]-2,3-dihydro-5-[2-(dimethylamino)ethyl]-2-(4-methoxyphenyl)naphtho[1,2-b][1,4]thiazepin-4(5H)-one, or the hydrochloride salt thereof.

21. The compound in accordance with claim 13, (±)-cis-2,3-dihydro-3-[[4-hydroxy-3,5-bis(1,1-dimethylethyl)benzoyl]oxy]-2-(4-methoxyphenyl)-5-[2-(dimethylamino)ethyl]naphtho[1,2-b][1,4]thiazepin-4(5H)-one, or the hydrochloride salt thereof.

22. The compound in accordance with claim 13, (±)-cis-2,3-dihydro-3-[4-[[[4-hydroxy-3,5-bis-(1,1-dimethylethyl)benzoyl]oxy]-bis-3,5-(1,1-dimethylethyl)-benzoyl]oxy]-5-[2-dimethylamino)ethyl]-2-(4-methoxyphenyl)naphtho[1,2-b][1,4]thiazepin-4(5H)-one, or the (E)-2-butenedioate salt thereof.

23. The compound in accordance with claim 13, [(±)-cis-3(2α or 2β)-2,3-dihydro-3-[[[3,4-dihydro-6-hydroxy-2-methyl-5,7-bis(1-methylethyl)-2H-1-benzopyran-2-yl]carbonyl]oxy]-5-[2-dimethylamino)ethyl]-2-(4-methoxyphenyl)naphtho[1,2-b][1,4]thiazepin-4(5H)-one, or the (E)-2-butenedioate salt thereof (isomer "A").

24. The compound in accordance with claim 13, [(±)-cis-3(2α or 2β)]-2,3-dihydro-3-[[[3,4-dihydro-6-hydroxy-2-methyl-5,7-bis(1-methylethyl)-2H-1-benzopyran-2-yl]carbonyl]oxy]-5-[2-(dimethylamino)ethyl]-2-(4-methoxyphenyl)naphtho[1,2-b][1,4]thiazepin-4(5H)-one, or the hydrochloride salt thereof. (Isomer "B").

25. A composition with calcium antogonistic activity comprising an effective amount of a (+)-cis compound of the formula

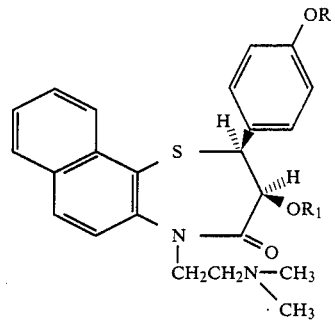

wherein R is lower alkyl; $R_1$ is

wherein $R_3$ is pyridyl,

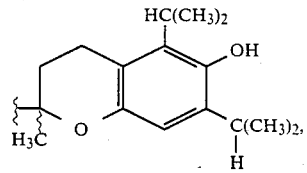

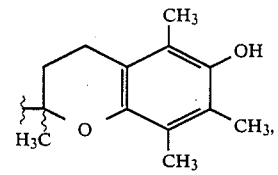

-continued

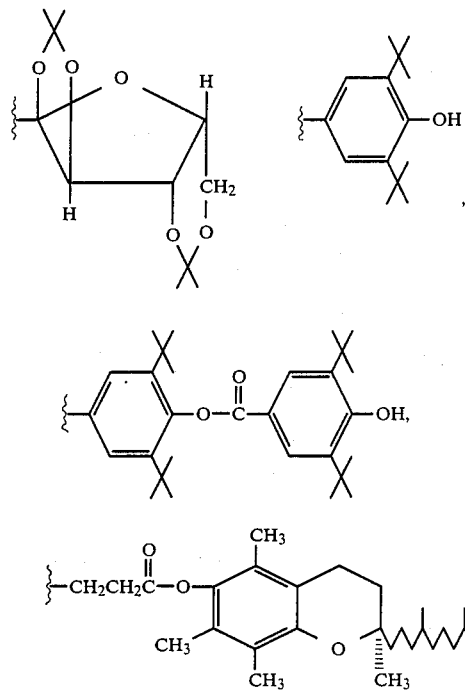

or phenyl unsubstituted or substituted by up to 3 substituents selected from the group consisting of hydroxy, halogen, lower alkoxy, and lower alkanoyloxy;
a (—)cis enantiomer, or a (±)-cis racemate thereof; or a pharmaceutically acceptable acid addition salt thereof, and a pharmaceutically inert carrier material.

26. A composition in accordance with claim 25, comprising an effective amount of a (+)-cis compound of the formula

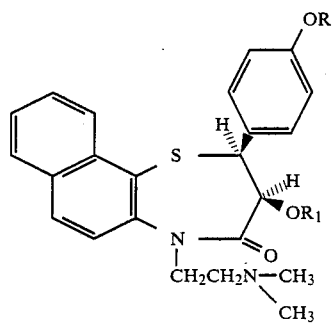

I wherein R is lower alkyl; $R_1$ is

wherein $R_3$ is pyridyl,

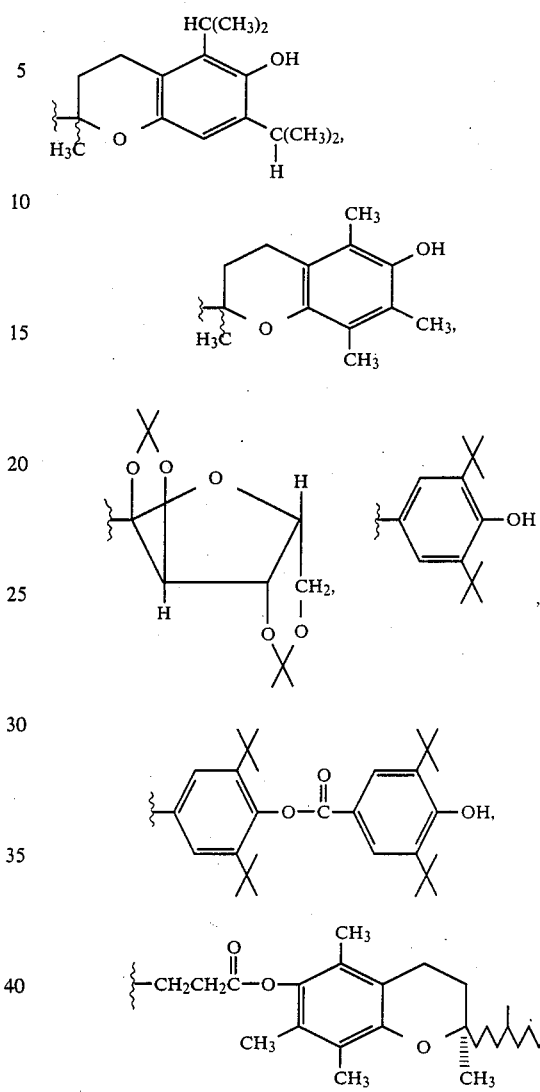

or phenyl unsubstituted or substituted by up to 3 substituents selected from the group consisting of hydroxy, halogen, lower alkoxy, and lower alkanoyloxy;
or a pharmaceutically acceptable acid addition salt thereof.

27. A composition in accordance with claim 26, wherein R is methyl.

28. A composition in accordance with claim 27, wherein the compound of formula I is (+)-cis-2,3-dihydro-3-[(3,4-dimethoxybenzoyl)oxy]-2-(4-methoxyphenyl)-5-[2-(dimethylamino)ethyl]naphtho[1,2-b][1,4]thiazepin-4(5H)-one, the semihydrate thereof, or the (E)-2-butenedioate hydrate thereof.

* * * * *